United States Patent [19]

Buzzetti et al.

[11] Patent Number: 5,652,250

[45] Date of Patent: Jul. 29, 1997

[54] N-SUBSTITUTED β-ARYL- AND β-HETEROARYL-α-CYANOACRYLAMIDE DERIVATIVES AND PROCESS FOR THEIR PREPARATION

[75] Inventors: Franco Buzzetti, Milan; Angelo Crugnola, Varese; Antonio Longo, Milan; Maria Gabriella Brasca, Milan; Dario Ballinari, Milan, all of Italy

[73] Assignee: Pharmacia S.p.A., Milan, Italy

[21] Appl. No.: 537,947

[22] PCT Filed: Mar. 2, 1995

[86] PCT No.: PCT/EP95/00758

§ 371 Date: Nov. 21, 1995

§ 102(e) Date: Nov. 21, 1995

[87] PCT Pub. No.: WO95/26341

PCT Pub. Date: Oct. 5, 1995

[30] Foreign Application Priority Data

Mar. 28, 1994 [GB] United Kingdom ............... 9406137

[51] Int. Cl.$^6$ ............... C07D 215/26; C07C 255/41; A61K 31/33
[52] U.S. Cl. ............... 514/352; 514/357; 514/447; 514/438; 514/613; 546/141; 546/142; 546/143; 546/145; 546/153; 546/155; 546/159; 546/164; 548/465; 548/483; 548/505; 564/164; 564/166; 564/167; 564/168
[58] Field of Search ............... 546/141, 142, 546/143, 145, 153, 155, 164; 548/465, 483, 505; 564/164, 166, 167, 168; 514/352, 357, 447, 438, 613

[56] References Cited

U.S. PATENT DOCUMENTS

| | | | |
|---|---|---|---|
| 5,122,537 | 6/1992 | Buzzetti et al. | 514/510 |
| 5,130,472 | 7/1992 | Buzzetti et al. | 560/252 |
| 5,196,446 | 3/1993 | Levitzki et al. | 514/415 |
| 5,397,787 | 3/1995 | Buzzetti et al. | 514/300 |
| 5,409,949 | 4/1995 | Buzzetti et al. | 514/414 |
| 5,436,235 | 7/1995 | Buzzetti et al. | 514/92 |
| 5,488,057 | 1/1996 | Buzzetti et al. | 514/312 |

FOREIGN PATENT DOCUMENTS

| | | |
|---|---|---|
| 537742 | 4/1993 | European Pat. Off. |
| 91/13055 | 9/1991 | WIPO |
| 91/16305 | 10/1991 | WIPO |

OTHER PUBLICATIONS

Ryabova, S.Y., Alekseeva, L.M., Granik, V.G. "Acetals of lactams and acid amides". 70. Reaction of 2-(aminomethylene)indolin-3-one derivatives with CH-acids. Synthesis of substituted pyrrolo[1,2-a]indoles. Khim. Geterotsikl. Soedin. 9, pp. 1199–1204, 1 1991.

Primary Examiner—Alan L. Rotman
Assistant Examiner—Lyman H. Smith
Attorney, Agent, or Firm—Oblon, Spivak, McClelland, Maier & Neustadt, P.C.

[57] ABSTRACT

The present invention relates to new compounds of formula

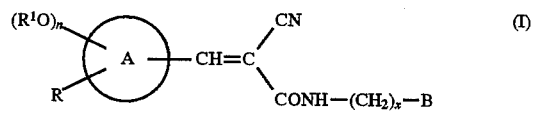

wherein
A is a bicyclic ring chosen from naphthalene, tetrahydronaphthalene, quinoline, isoquinoline and indole.
B is a $R^2$ substituted benzene ring or an unsubstituted pyridine or thiophene ring;
R is hydrogen, $C_1$–$C_6$ alkyl, halogen, nitro, cyano, carboxy or a group $NR^3R^4$ wherein each of $R^3$ and $R^4$ is independently hydrogen or $C_1$–$C_6$ alkyl;
$R^1$ is hydrogen, $C_1$–$C_6$ alkyl or $C_1$–$C_6$ alkanoyl;
$R^2$ is hydrogen, $C_1$–$C_6$ alkyl, halogen, nitro, cyano, carboxy, hydroxy, $C_1$–$C_6$ alkoxy, $C_1$–$C_6$ alkanoyloxy or a group $NR^3R^4$ wherein $R^3$ and $R^4$ are as defined above;
n is zero or an integer of 1 to 2;
x is zero or an integer of 1 to 5;
and the pharmaceutically acceptable salts thereof.

The compounds of the invention are useful as tyrosine kinase inhibitors.

10 Claims, No Drawings

N-SUBSTITUTED β-ARYL- AND β-HETEROARYL-α-CYANOACRYLAMIDE DERIVATIVES AND PROCESS FOR THEIR PREPARATION

This application is a 35 USC 371 National Stage filing of PCT/EP95/00758 published as WO 95/26341 on Oct. 5, 1995.

The present invention relates to new N-substituted β-aryl- and β-heteroaryl-α-cyanoacrylamide derivatives to a process for their preparation, to pharmaceutical compositions containing them and to their use as therapeutic agents.

The present invention provides compounds having the following general formula (I)

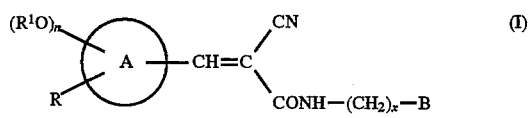

wherein
A is a bicyclic ring chosen from naphthalene, tetrahydronaphthalene, quinoline, isoquinoline and indole;
B is a $R^2$ substituted benzene ring or an unsubstituted pyridine or thiophene ring;
R is hydrogen, $C_1$–$C_6$ alkyl, halogen, nitro, cyano, carboxy or a group $NR^3R^4$ wherein each of $R^3$ and $R^4$ is independently hydrogen or $C_1$–$C_6$ alkyl;
$R^1$ is hydrogen, $C_1$–$C_6$ alkyl or $C_1$–$C_6$ alkanoyl;
$R^2$ is hydrogen, $C_1$–$C_6$ alkyl, halogen, nitro, cyano, carboxy, hydroxy, $C_1$–$C_6$ alkoxy, $C_1$–$C_6$ alkanoyloxy, or a group $NR^3R^4$ wherein $R^3$ and $R^4$ are as defined above;
n is zero or an integer of 1 to 2;
x is zero or an integer of 1 to 5;
and the pharmaceutically acceptable salts thereof.

In the compounds of formula (I) when A is naphthalene, quinoline, isoquinoline or indole, then each of the substituents R and OR' may be independently on either of the two rings constituting the bicyclic system, when A is tetrahydronaphthalene whilst they are only on the benzene ring of the bicyclic system.

When n is 2, the OR' groups may be the same or different.

The invention includes within its scope all the possible isomers, stereoisomers, in particular Z and E isomers and their mixtures, and the metabolites and the metabolic precursors or bio-precursors (otherwise known as pro-drugs) of the compounds of formula (I).

The alkyl groups and the alkyl moieties in the alkoxy, alkanoyl or alkanoyloxy groups may be branched or straight alkyl chains.

A $C_1$–$C_6$ alkyl is preferably a $C_1$–$C_4$ alkyl, e.g. methyl, ethyl, propyl, isopropyl, butyl, sec-butyl or tert-butyl, in particular methyl or ethyl.

A $C_1$–$C_6$ alkoxy group is preferably a $C_1$–$C_3$ alkoxy, in particular methoxy.

A $C_1$–$C_6$ alkanoyl group is preferably a $C_2$–$C_3$ alkanoyl group, in particular acetyl or propionyl.

A $C_1$–$C_6$ alkanoyloxy group is preferably a $C_2$–$C_3$ alkanoyloxy group, in particular acetyloxy or propionyloxy.

A halogen is preferably fluorine, chlorine or bromine, in particular fluorine or chlorine.

A group

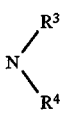

is, preferably, amino.

Under tetrahydronaphthalene more precisely we intend 5,6,7,8-tetrahydronaphthalene.

When A is naphthalene the R and $R^1O$ substituents and the acrylamide side chain are preferably on the same benzene moiety.

When A is 5,6,7,8-tetrahydronaphthalene the R and $R^1O$ substituent and the acrylamide side chain are preferably on the aromatic benzene moiety.

When A is quinoline the acrylamide side chain is preferably attached to the 4- or 5-position of the quinoline ring and the R and $R^1O$ substituents are preferably on the same aryl or heteroaryl moiety of said ring.

When A is isoquinoline the acrylamide side chain is preferably attached to the 3 or 5-position of the isoquinoline ring and the R and $R^1O$ substituents are preferably on the benzene moiety of said ring.

When A is indole ring the acrylamide side chain is preferably attached to the pyrrole moiety and the R and $R^1O$ substituents are preferably on the benzene moiety of said ring. In this case preferably A is a 3-indolyl group.

Of course only one of the substituents R, $R^1O$ and acrylamide side chain can be linked to the same carbon of the A ring.

The $R^2$ substituent is preferably in para position on the benzene ring.

When one of R and $R^2$ is $NO_2$, COOH or $NR^3R^4$, then the other has preferably a different meaning.

Pharmaceutically acceptable salts of the compounds of the invention include acid addition salts, with inorganic acids, e.g. hydrochloric, sulphuric, perchloric and phosphoric acid, or organic acids, e.g. acetic, glycolic, lactic, oxalic, malonic, malic, maleic, tartaric, citric, benzoic, cinnamic, mandelic and salicylic acid, and salts with inorganic bases, e.g. sodium, potassium, calcium or magnesium base, or with organic bases, e.g. alkylamines, preferably triethylamine.

As stated above, the present invention also includes within its scope pharmaceutically acceptable bio-precursors (otherwise known as pro-drugs) of the compounds of formula (I), i.e. compounds which have a different formula to formula (I) above, but which nevertheless upon administration to human being are converted directly or indirectly in vivo into a compound of formula (I).

Preferred compounds of the invention are the compounds of formula (I), wherein
A is tetrahydronaphthalene, quinoline, isoquinoline and indole;
B is $R^2$ substituted benzene or unsubstituted pyridine;
R is hydrogen or halogen with the exception of indole derivatives where R can also be carboxy or amino;
$R^1$ is hydrogen or methyl;
$R^2$ is hydrogen, halogen, cyano, hydroxy, carboxy or amino;
n is 0, 1 or 2 and
x is 0, 1, 2 or 3;
and the pharmaceutically acceptable salts thereof.

A particularly preferred class of compounds of the invention are the compounds of formula (I) in which
A is tetrahydronaphthalene, quinoline, isoquinoline and indole;
B is $R^2$ substituted benzene or an unsubstituted pyridine;

R is hydrogen with the exception of indole derivatives where R can also be carboxy or amino;
$R^1$ is hydrogen or methyl;
$R^2$ is hydrogen or hydroxy;
n is 0, 1 or 2; and
x is 0, or 2;
and the pharmaceutically acceptable salts thereof.

More preferably the $OR^1$ substituents are linked to position 3 and 4 when A is 5,6,7,8-tetrahydronaphth-1-yl and to position 4 when A is 5,6,7,8-tetrahydronaphth-2-yl. When A is quinoline the $OR^1$ substituent is more preferably linked to position 8. When A is indole the R or $OR^1$ substituent is more preferably linked to position 5. In all above mentioned cases the $R^2$ substituent is more preferably linked to position 4'.

Examples of specific compounds of the invention are the following compounds, which, may be either Z- or E-isomers or Z,E-mixtures of said isomers:

N-phenyl β-(4-hydroxy-5,6,7,8-tetrahydronaphth-1-yl)-α-cyanoacrylamide;
N-(4'-hydroxyphenyl)-β-(4-hydroxy-5,6,7,8-tetrahydronaphth-1-yl)-α-cyanoacrylamide;
N-phenyl β-(3,4-dihydroxy-5,6,7,8-tetrahydronaphth-1-yl)-α-cyanoacrylamide;
N-(4'-hydroxyphenyl) β-(3,4-dihydroxy-5,6,7,8-tetrahydronaphth-1-yl)-α-cyanoacrylamide;
N-benzyl β-(4-hydroxy-5,6,7,8-tetrahydronaphth-1-yl)-α-cyanoacrylamide;
N-(4'-hydroxybenzyl) β-(4-hydroxy-5,6,7,8-tetrahydronaphth-1-yl)-α-cyanoacrylamide;
N-benzyl β-(3,4-dihydroxy-5,6,7,8-tetrahydronaphth-1-yl)-α-cyanoacrylamide;
N-(4'-hydroxybenzyl) β-(3,4-dihydroxy-5,6,7,8-tetrahydronaphth-1-yl)-α-cyanoacrylamide;
N-phenethyl β-(4-hydroxy-5,6,7,8-tetrahydronaphth-1-yl)-α-cyanoacrylamide;
N-(4'-hydroxyphenethyl) β-(4-hydroxy-5,6,7,8-tetrahydronaphth-1-yl)-α-cyanoacrylamide;
N-phenethyl β-(3,4-dihydroxy-5,6,7,8-tetrahydronaphth-1-yl)-α-cyanoacrylamide;
N-(4'-hydroxyphenethyl) β-(3,4-dihydroxy-5,6,7,8-tetrahydronaphth-1-yl)-α-cyanoacrylamide;
N-phenyl β-(4-hydroxy-5,6,7,8-tetrahydronaphth-2-yl)-α-cyanoacrylamide;
N-(4'-hydroxyphenyl) β-(4-hydroxy-5,6,7,8-tetrahydronaphth-2-yl)-α-cyanoacrylamide;
N-benzyl β-(4-hydroxy-5,6,7,8-tetrahydronaphth-2-yl)-α-cyanoacrylamide;
N-(4'-hydroxybenzyl) β-(4-hydroxy-5,6,7,8-tetrahydronaphth-2-yl)-α-cyanoacrylamide;
N-phenethyl β-(4-hydroxy-5,6,7,8-tetrahydronaphth-2-yl)-α-cyanoacrylamide;
N-(4'-hydroxyphenethyl) β-(4-hydroxy-5,6,7,8-tetrahydronaphth-2-yl)-α-cyanoacrylamide;
N-phenyl β-(4-quinolyl)-α-cyanoacrylamide;
N-(4'-hydroxyphenyl) β-(4-quinolyl)-α-cyanoacrylamide;
N-benzyl β-(4-quinolyl)-α-cyanoacrylamide;
N-(4'-hydroxybenzyl) β-(4-quinolyl)-α-cyanoacrylamide;
N-phenethyl β-(4-quinolyl)-α-cyanoacrylamide;
N-(4'-hydroxyphenethyl) β-(4-quinolyl)-α-cyanoacrylamide;
N-phenyl β-(8-hydroxy-5-quinolyl)-α-cyanoacrylamide;
N-(4'-hydroxyphenyl) β-(8-hydroxy-5-quinolyl)-α-cyanoacrylamide;
N-benzyl β-(8-hydroxy-5-quinolyl)-α-cyanoacrylamide;
N-(4'-hydroxybenzyl) β-(8-hydroxy-5-quinolyl)-α-cyanoacrylamide;
N-phenethyl β-(8-hydroxy-5-quinolyl)-α-cyanoacrylamide;
N-(4'-hydroxyphenethyl) β-(8-hydroxy-5-quinolyl)-α-cyanoacrylamide;
N-phenyl β-(3-isoquinolyl)-α-cyanoacrylamide;
N-(4'-hydroxyphenyl) β-(3-isoquinolyl)-α-cyanoacrylamide;
N-benzyl β-(3-isoquinolyl)-α-cyanoacrylamide;
N-(4'-hydroxybenzyl) β-(3-isoquinolyl)-α-cyanoacrylamide;
N-phenethyl β-(3-isoquinolyl)-α-cyanoacrylamide;
N-(4'-hydroxyphenethyl) β-(3-isoquinolyl)-α-cyanoacrylamide;
N-phenyl β-(5-isoquinolyl)-α-cyanoacrylamide;
N-(4-hydroxyphenyl) β-(5-isoquinolyl)-α-cyanoacrylamide;
N-benzyl β-(5-isoquinolyl)-α-cyanoacrylamide;
N-(4'-hydroxybenzyl) β-(5-isoquinolyl)-α-cyanoacrylamide;
N-phenethyl β-(5-isoquinolyl)-α-cyanoacrylamide;
N-(4'-hydroxyphenethyl) β-(5-isoquinolyl)-α-cyanoacrylamide;
N-phenyl β-(3-indolyl)-α-cyanoacrylamide;
N-benzyl β-(3-indolyl)-α-cyanoacrylamide;
N-phenethyl β-(3-indolyl)-α-cyanoacrylamide;
N-phenyl β-(5-hydroxy-3-indolyl)-α-cyanoacrylamide;
N-benzyl β-(5-hydroxy-3-indolyl)-α-cyanoacrylamide;
N-phenethyl β-(5-hydroxy-3-indolyl)-α-cyanoacrylamide;
N-phenyl β-(5-carboxy-3-indolyl)-α-cyanoacrylamide;
N-benzyl β-(5-carboxy-3-indolyl)-α-cyanoacrylamide;
N-phenethyl β-(5-carboxy-3-indolyl)-α-cyanoacrylamide;
N-phenyl β-(5-amino-3-indolyl)-α-cyanoacrylamide;
N-benzyl β-(5-amino-3-indolyl)-α-cyanoacrylamide;
N-phenethyl β-(5-amino-3-indolyl)-α-cyanoacrylamide;
N-(4'-hydroxyphenyl) β-(3-indolyl)-α-cyanoacrylamide;
N-(4'-hydroxybenzyl) β-(3-indolyl)-α-cyanoacrylamide;
N-(4'-hydroxyphenethyl) β-(3-indolyl)-α-cyanoacrylamide;
N-(4'-hydroxyphenyl) β-(5-hydroxy-3-indolyl)-α-cyanoacrylamide;
N-(4'-hydroxybenzyl) β-(5-hydroxy-3-indolyl)-α-cyanoacrylamide;
N-(4'-hydroxyphenethyl) β-(5-hydroxy-3-indolyl)-α-cyanoacrylamide;
N-(4'-hydroxyphenyl) β-(5-carboxy-3-indolyl)-α-cyanoacrylamide;
N-(4'-hydroxybenzyl) β-(5-carboxy-3-indolyl)-α-cyanoacrylamide;
N-(4'-hydroxyphenethyl) β-(5-carboxy-3-indolyl)-α-cyanoacrylamide;
N-(4'-hydroxyphenyl) β-(5-amino-3-indolyl)-α-cyanoacrylamide;
N-(4'-hydroxybenzyl) β-(5-amino-3-indolyl)-α-cyanoacrylamide;
N-(4'-hydroxyphenethyl) β-(5-amino-3-indolyl)-α-cyanoacrylamide;
N-phenyl β-(5-methoxy-3-indolyl)-α-cyanoacrylamide;
N-benzyl β-(5-methoxy-3-indolyl)-α-cyanoacrylamide;
N-(3-pyridyl) β-(4-hydroxy-5,6,7,8-tetrahydronaphth-1-yl)-α-cyanoacrylamide;
N-(3-pyridyl) β-(3-indolyl)-α-cyanoacrylamide;
N-(3-pyridyl) β-(5-methoxy-3-indolyl)-α-cyanoacrylamide;
N-(3-pyridyl) β-(4-quinolyl)-α-cyanoacrylamide;
N-(3-pyridylmethyl) β-(4-hydroxy-5,6,7,8-tetrahydronaphth-1-yl)-α-cyanoacrylamide;
N-(3-pyridylmethyl) β-(3-indolyl)-α-cyanoacrylamide;
N-(3-pyridylmethyl) β-(5-methoxy-3-indolyl)-α-cyanoacrylamide;
N-(3-pyridylmethyl) β-(4-quinolyl)-α-cyanoacrylamide;

N-(2-pyridylmethyl) β-(4-hydroxy-5,6,7,8-tetrahydronaph-1-yl)-α-cyanoacrylamide;

N-(2-pyridylmethyl) β-(3-indolyl)-α-cyanoacrylamide;

N-(2-pyridylmethyl) β-(5-methoxy-3-indoyl)-α-cyanoacrylamide;

N-(2-pyridylmethyl) β-(4-quinolyl)-α-cyanoacrylamide, and, when appropriate, the pharmaceutically acceptable salts thereof.

The compounds of the invention, and the pharmaceutically acceptable salts thereof, can be obtained by a process comprising the condensation of an aldehyde of formula (II)

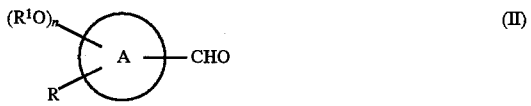

wherein A, R, $R^1$ and n are as defined above, with a compound of formula (III)

$$NC-CH_2-CONH-(CH_2)_x-B \qquad (III)$$

wherein $R^2$ and x are as defined above, and, if desired, converting a compound of formula (I) into another compound of formula (I), and/or, if desired, converting a compound of formula (I) into a pharmaceutically acceptable salt thereof, and/or, if desired, converting a salt into a free compound, and/or, if desired, separating a mixture of isomers of a compound of formula (I) into the single isomers.

Each of the substituents R, $R^1O$ and —CHO in a compound of formula (II) may be independently on either of the rings in naphthalene, quinoline, isoquinoline and indole, whilst in the case of tetrahydronaphthalene they are preferably on the same aromatic ring.

The condensation of a compound of formula (II) with a compound of formula (III) may be carried out according to known methods as herebelow described. For example it may be carried out under the conditions of the Knoevanagel reaction as described, e.g., by G. Jones in Organic Reactions 15, 204(1967).

Suitable catalysts are organic bases such as pyridine, piperidine or diethylamine. The condensation may be performed in an inert organic solvent, e.g., pyridine, ethanol; methanol, benzene or dioxane at temperatures ranging from about 0° C. to about 100° C. Preferably the reaction is carried out in hot ethanol solution in the presence of piperidine catalyst.

A compound of formula (I) can be converted into another compound of formula (I) according to known methods. For example the de-etherification of a compound of formula (I) wherein $R^1O$ is methoxy, so as to obtain a compound of formula (I) wherein $R^1O$ is hydroxy, can be carried out for example with boron tribromide as described by J. F. N. McOmie in Tetrahedron 24, 2289 (1968). The reaction may be performed in an inert organic solvent such as dichloromethane or benzene under an inert atmosphere (e.g. nitrogen) at temperatures ranging from about −78° C. to about room temperature.

The conversion of a compound of formula (I) in which R or $R^2$ is nitro into the corresponding compound of formula (I), wherein R or $R^2$ is amino, may be carried out following known methods, for example with a variety of reducing agents, e.g. sodium sulfide in hydroalcoholic solution, metallic iron with ammonium chloride in aqueous solvent, or for instance, catalytic hydrogenation using e.g. palladium charcoal catalyst at low hydrogen pressure in an inert organic solvent.

The alkylation of a compound of formula (I), wherein $R^1O$ or $R^2$ is hydroxy, so as to obtain the corresponding compound of formula (I), wherein $R^1O$ or $R^2$ is $C_1-C_6$ alkoxy, may be obtained, e.g., by reaction with sodium hydride and $C_1-C_6$ alkyl iodide in a high boiling aromatic solvent such as xylene.

The acylation of a compound of formula (I), wherein $R^2$ or $R^1O$ is hydroxy, in order to obtain the corresponding compound of formula (I), wherein $R^2$ or $R^1O$ is a $C_1-C_6$ alkanoyloxy, can be performed, e.g., by reaction with a suitable carboxylic acid anhydride in the presence of a basic agent at temperatures ranging from room temperature to reflux temperatures.

The optional salification of a compound of formula (I) as well as the conversion of a salt into a free compound, and the separation of a mixture of isomers into the single isomers may be carried out by conventional methods. For example the separation of a mixture of geometric isomers, e.g., cis- and trans-isomers, may be carried out by fractional crystallization from a suitable solvent or by chromatography, either column chromatography or HPLC.

The compounds of formula (II) may be obtained according to known methods from compounds of formula (IV)

wherein A, R and $R^1$ are as defined above.

For example when compound (IV) contains phenolic groups, i.e. $R^1O$ is hydroxy, the well known Reimer-Tiemann method can be applied. Thus the phenolic compound is treated with chloroform and alkali hydroxides in an aqueous or hydroalcoholic solution. Another useful method for the synthesis of aromatic or phenolic aldehydes has been described by H. Gross et al. in Chem. Ber. 96, 308 (1963). Accordingly a compound of formula (IV), in which the $OR^1$ group may be present or not, can be treated with a dichloromethyl ether, e.g. dichloromethyl methyl ether, in the presence of a Friedel-Crafts catalyst such as titanium tetrachloride or aluminium trichloride in an inert solvent like dichloromethane or nitrobenzene at temperatures ranging from about 0° C. to about 60° C.

3-Formylindole derivatives of formula (II) can be obtained for example from compounds of formula (IV) by formylation with N-methylformanilide and phosphorus oxychloride according to the well known Vilsmeyer-Haack method [for a review see W. G. Jackson et al. in J. Am. Chem. Soc. 103, 523 (1981)].

The compounds of formula (III) may be obtained by known methods from a compound of formula (V)

$$CN-CH_2-COOR^5 \qquad (V)$$

wherein $R^5$ is a $C_1-C_6$ alkyl group, in particular a methyl group, by condensation with a compound of formula (VI)

$$H_2N-(CH_2)_x-B \qquad (VI)$$

wherein $R^2$ and x are as defined above.

Preferably the condensation is carried out by heating equimolar amounts of compound (VI) and compound (V) in the form of its methylester at temperatures ranging from about 100° C. to 200° C. for several hours without adding a solvent.

Alternatively a compound of formula (III) can be obtained by reacting a compound of formula (V) wherein $R^5$ is H with a compound of formula (VI) wherein β and X are as defined above using dicyclohexylcarbodiimide as coupling agent and conducting the reaction in an inert solvent such as THF or benzene at temperatures ranging from room to reflux temperatures.

The compounds of formulae (IV), (V) and (VI) are known or can be obtained by known methods.

When in the compounds of formula (I) and in the intermediate products thereof groups are present which need to be protected before submitting them to hereabove illustrated reactions, they may be protected before the reaction take place and then deprotected at the end of the reaction, according to well known methods in organic chemistry.

PHARMACOLOGY

The compounds of the invention possess specific tyrosine kinase inhibiting activity. It is believed that tyrosine kinase inhibitors may be of great importance in the control of uncontrolled cellular reproduction, i.e. in cellular reproduction disorders. Hence the compounds according to the present invention can be useful in the treatment of pathological proliferation disorders in mammals, including humans. They can be useful e.g. in the treatment of benign and malign tumors. They are able to cause tumor regression and to prevent tumor metastasis and the growth of micrometastasis.

Moreover they can also be useful for the treatment of leukemia and psoriasis. They have also utility in the control of immune system diseases (immunosuppressants), angiogenesis and atherosclerosis (atheromatous plaque) as far as protein kinases are involved in these diseases.

Recent studies on the molecular basis of neoplastic transformation have identified a family of genes, designed oncogenes, whose aberrant expression causes tumorigenesis. For example, the RNA tumor viruses possess such an oncogene sequence whose expression determines neoplastic conversion of infected cells. Several of their oncogene-encoded proteins, such as $pp60^{v\text{-}src}$, $p70^{gag\text{-}yes}$, $p130^{gag\text{-}fps}$ and $p70^{gag\text{-}fgr}$ display protein tyrosine kinase activity, that is they catalyze the transfer of the γ-phosphate from adenosine triphosphate (ATP) to tyrosine residues in protein substrate. In normal cells, several growth factor receptors, for example the receptors for PDGF, EGF, α-TGF and insulin, display tyrosine kinase activity.

Binding of the growth factor (GF) activates the receptor tyrosine kinase to undergo autophosphorylation and to phosphorylate closely adjacent molecules on tyrosine.

Therefore, it is thought that the phosphorylation of these tyrosine kinase receptors plays an important role in signal transduction and that the principal function of tyrosine kinase activity in normal cells is to regulate cell growth. Perturbation of this activity by oncogenic tyrosine kinases that are either overproduced and/or display altered substrate specificity may cause loss of growth control and/or neoplastic transformation. Accordingly, a specific inhibitor of tyrosine kinases can be useful in investigating the mechanism of carcinogenesis, cell proliferation and differentiation and it can be effective in prevention and chemotherapy of cancer and other pathological proliferative conditions.

In particular the compounds of the invention can be used in the treatment of cancers, metastasis, leukemia, psoriasis, angiogenesis, atherosclerosis (atheromatous plaque) and immune system diseases as far as protein kinases are involved in these diseases.

The tyrosine specific protein kinase activity of the compounds of the invention is shown, e.g., by the fact that they are active in the in-vitro and in-vivo test described herebelow.

In-vitro Assay p45 v-abl Kinase Purification

The enzyme used in our test was the p45 v-abl tyrosine kinase which represents the catalytic domain of the Abelson tyrosine kinase (isolated from the Abelson murine leukemia virus). The p45 v-abl kinase was produced and isolated as described by Wang et al. in J. Biol. Chem. 260, 64 (1985) and by Ferguson et al. in J. Biol. Chem. 260, 3652 (1985) and in Biochem. J. 257, 321 (1989).

p45 v-abl Kinase Assay (Val$^5$)-Angiotensin II phosphorylation was performed by incubation with 40 ng of purified abl-kinase and ($\gamma^{32}$P)-ATP, in 50 μl of buffer containing Tris-HCl 25 mM, pH 8.0, MgCl$_2$ 10 mM and dithiothreitol 0.1 mM (kinase buffer). The reaction mixture was incubated for the indicated time at 30° C. and the reaction stopped by adding 50 μl of 5% trichloroacetic acid. After a brief incubation on ice, tubes were centrifuged. The supernatants were spotted on phosphocellulose paper squares (Whatman P-81) and washed extensively in acetic acid. The radioactivity bound to dried phosphocellulose squares was measured in a liquid scintillation counter. IC$_{50}$ values were calculated from triplicate determinations of each experimental point. Each inhibitor was tested at concentrations ranging from 0 to 400 μg in the presence of fixed concentrations of peptide (2 mM) and ATP (50 μM).

In-vivo Assay

K562 Cell Growth Inhibition Assay

K562 cells, a human myelogenous leukemia cell line, were seeded into a 24 wells tissue culture plate (Falcon 3047) (10000/well) in the presence of increasing concentrations of the compounds. After 72 h, cells were harvested and were counted using a cell counter (Coulter Counter—ZM). The percent of inhibition was evaluated in respect to the untreated control cells.

The inhibitory activity data for a representative compound according to the present invention, obtained both in the in-vitro p45 v-abl kinase assay and in the in-vivo human chronic myeloid leukemia K562 cell growth inhibition assay described above, are set out in Table 1.

TABLE I

Inhibition of p45 v-abl kinase and K562 cell growth

| | IC$_{50}$ (μM) | |
|---|---|---|
| | v-abl | K562 |
| N-phenyl β-(8-hydroxy-5-quinolyl)-α-cyanoacrylamide | 3.4 | 0.66 |

In view of their high activity and low toxicity, the compounds of the invention can be used safely in medicine.

For example, the approximate acute toxicity (LD$_{50}$) of the compounds of the invention in the mouse, determined by single administration of increasing doses and measured on the seventh day after the treatment was found to be negligible.

The compounds of the invention can be administered in a variety of dosage forms, e.g. orally, in the form of tablets, capsules, sugar- or film-coated tablets, liquid solutions or suspensions, rectally, in the form of suppositories; parenterally, e.g. intramuscularly, or by intravenous injection or infusion; or topically.

The dosage depends on the age, weight, condition of the patient and administration route; for example, the dosage adopted for oral administration to adult humans may range from about 10 to about 150–200 mg per dose, from 1 to 5 times daily. Of course, these dosage regimens may be adjusted to provide the optimal therapeutic response.

The invention includes pharmaceutical compositions comprising a compound of formula (I) or a pharmaceutically acceptable salt thereof in association with a pharmaceutically acceptable excipient, which can be a carrier or diluent.

The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate, effervescing mixtures; dyestuffs; sweeteners; wetting agents, such as lecithin, polysorbates, lauryl-sulphates; and, in general, non-toxic and pharmacologically inactive substances used in pharmaceutical formulations. Said pharmaceutical preparations may be manufactured in known manner, for example, by means of mixing, granulating, tabletting, sugar-coating or film-coating processes.

The liquid dispersion for oral administration may be e.g. syrups, emulsions and suspensions.

The syrup may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethyl-cellulose or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride.

The solutions for intravenous injections or infusion may contain as carrier, for example, sterile water or, preferably, they may be in the form of sterile, aqueous, isotonic saline solutions.

The suppositories may contain, together with the active compound, a pharmaceutically acceptable carrier, e.g. cocoa-butter, polyethylene glycol, a polyoxyethylene sorbitan fatty acid ester surfactant or lecithin.

Compositions for topical application, e.g. creams, lotions, or pastes, can be prepared by admixing the active ingredient with a conventional oleaginous or emulsifying excipient.

A further object of the present invention is a combined method of treatment of cancer in mammals, including humans, in need of such treatment, said method comprising administering 1) a compound of formula (I), or a pharmaceutically acceptable salt thereof, and
2) an additional antitumor agent, in amounts and close enough together in time sufficient to produce a therapeutically useful effect.

Object of the present invention is also to provide products containing a compound of formula (I), or a pharmaceutically acceptable salt, and an additional antitumor agent as a combined preparation for simultaneous, separate or sequential use in anti-cancer therapy.

The term "antitumor agent" is meant to comprise both a single antitumor drug and "cocktails" i.e. a mixture of such drugs, according to the clinical practice.

Antitumor agents that can be formulated with a compound of the invention or alternatively, can be administered in a combined method of treatment, are e.g. doxorubicin, daunomycin, epirubicin, idarubicin, etoposide, fluorouracil, melphalan, cyclophosphamide, bleomycin, vinblastin and mitomycin or a mixture of two or more thereof.

The compounds of the invention can therefore be used in a treatment to ameliorate a cancer pathology. They may be administered to a patient suffering from a cancer treatable with an antitumor agent, for example an anthracycline glycoside such as doxorubicin, daunomycin, epirubicin or idarubicin as mentioned above, together with the antitumor agent.

A compound of the invention and an antitumor agent such as an anthracycline glycoside can be administered to improve the condition of a patient having a leukaemia such as myeloblastic leukaemia, lymphoma, sarcoma, neuroblastoma, Wilm's tumor or malignant neoplasm of the bladder, breast, lung or thyroid.

The following examples illustrate but do not limit the invention.

EXAMPLE 1

N-phenyl β-(8-hydroxy-5-quinolyl)-α-cyanoacrylamide

A solution of 8-hydroxy-5-quinolinecarboxaldehyde (1.732 g, 0.010 mol), N-phenyl cyanoacetamide (1.602 g, 0.010 mol) and piperidine (0.255 g, 0.003 mol) in absolute ethanol (50 ml) was heated for 3 h at reflux. The reaction mixture was chilled to about 10°–15° C., the precipitate filtered, the residue washed with ice-cooled ethanol and dried under vacuum. Almost pure title compound was obtained in about 75% yield (2.365 g).

Compounds of high purity are obtained by crystallization from ethanol.

$C_{19}H_{13}N_3O_2$ calculated: C 72.37 H 4.15 N 13.33 found: C 72.40 H 4.20 N 13.30

MS m/z 315.

IR $cm^{-1}$: 3300–3600 (NH,OH), 2210 (CN), 1680, 1600 (CONH), 1530, 1510 (C=C)

NMR δ ppm (DMSO): 7.0–7.5 (m, 4H), 7.6–7.8 (m, 3H), 8.36 (d, J=8.4 Hz, 1H), 8.80 (dd, J=1.4 and 8.6 Hz, 1H), 8.83 (s, 1H), 8.95 (dd, J=1.4 and 1.4 Hz, 1H), 10.4 (bs, 1H).

According to the above described procedure and starting from the appropriate compounds of formula (II) and of formula (III) one can prepare the following compounds as single E- or Z-isomers, as well as their E,Z-mixtures:

N-phenyl β-(4-hydroxy-5,6,7,8-tetrahydronaphth-1-yl)-α-cyanoacrylamide $C_{20}H_{18}N_2O_2$ calculated: C 75.45 H 5.70 N 8.80 found: C 75.35 H 5.65 N 8.75

MS m/z 318.

NMR δ ppm (DMSO): 1.77 (m, 4H), 2.55, 2.80 (two m, 4H), 6.78 (d, J=8.6 Hz, 1H), 7.11 (m, 1H), 7.34 (m, 2H), 7.64 (m, 2H), 7.80 (d, J=8.6 Hz, 1H), 8.31 (s, 1H), 10.18 (s, 1H), 10.3 (bs, 1H).

N-(4'-hydroxyphenyl)-β-(4-hydroxy-5,6,7,8-tetrahydronaphth-1-yl)-α-cyanoacrylamide;

N-phenyl β-(3,4-dihydroxy-5,6,7,8-tetrahydronaphth-1-yl)-α-cyanoacrylamide;
N-(4'-hydroxyphenyl) β-(3,4-dihydroxy-5,6,7,8-tetrahydronaphth-1-yl)-α-cyanoacrylamide;
N-benzyl β-(4'-hydroxy-5,6,7,8-tetrahydronaphth-1-yl)-α-cyanoacrylamide;
N-(4'-hydroxybenzyl) β-(4-hydroxy-5,6,7,8-tetrahydronaphth-1-yl)-α-cyanoacrylamide;
N-benzyl β-(3,4-dihydroxy-5,6,7,8-tetrahydronaphth-1-yl)-α-cyanoacrylamide;
N-(4'-hydroxybenzyl) β-(3,4-dihydroxy-5,6,7,8-tetrahydronaphth-1-yl)-α-cyanoacrylamide;
N-phenethyl-β-(4-hydroxy-5,6,7,8-tetrahydronaphth-1-yl)-α-cyanoacrylamide;
N-(4'-hydroxyphenethyl) β-(4-hydroxy-5,6,7,8-tetrahydronaphth-1-yl)-α-cyanoacrylamide;
N-phenethyl β-(3,4-dihydroxy-5,6,7,8-tetrahydronaphth-1-yl)-α-cyanoacrylamide;
N-(4'-hydroxyphenethyl) β-(3,4-dihydroxy-5,6,7,8-tetrahydronaphth-1-yl)-α-cyanoacrylamide;
N-phenyl β-(4-hydroxy-5,6,7,8-tetrahydronaphth-2-yl)-α-cyanoacrylamide;
N-(4'-hydroxyphenyl) β-(4-hydroxy-5,6,7,8-tetrahydronaphth-2-yl)-α-cyanoacrylamide;
N-benzyl β-(4-hydroxy-5,6,7,8-tetrahydronaphth-2-yl)-α-cyanoacrylamide;
N-(4'-hydroxybenzyl) β-(4-hydroxy-5,6,7,8-tetrahydronaphth-2-yl)-α-cyanoacrylamide;
N-phenethyl β-(4-hydroxy-5,6,7,8-tetrahydronaphth-2-yl)-α-cyanoacrylamide;
N-(4'-hydroxyphenethyl) β-(4-hydroxy-5,6,7,8-tetrahydronaphth-2-yl)-α-cyanoacrylamide;

N-phenyl β-(4-quinolyl)-α-cyanoacrylamide $C_{19}H_{13}N_3O$ calculated: C 76.24 H 4.38 N 14.04
MS m/z 299.
NMR δ ppm (DMSO): 7.17 v (m, 1H), 7.40 (m, 2H), 7.6–8.0 (m, 5H), 8.1–8.4 (m, 2H), 8.95 (s, 1H), 9.09 (d, J=4.4 Hz, 1H), 10.65 (s, 1H).

N-(4'-hydroxyphenyl) β-(4-quinolyl)-α-cyanoacrylamide;
N-benzyl β-(4-quinolyl)-α-cyanoacrylamide;
N-(4'-hydroxybenzyl) β-(4-quinolyl)-α-cyanoacrylamide;
N-phenethyl β-(4-quinolyl)-α-cyanoacrylamide;
N-(4'-hydroxyphenethyl) β-(4-quinolyl)-α-cyanoacrylamide;
N-(4'-hydroxyphenyl) β-(8-hydroxy-5-quinolyl)-α-cyanoacrylamide;
N-benzyl β-(8-hydroxy-5-quinolyl)-α-cyanoacrylamide;
N-(4'-hydroxybenzyl) β-(8-hydroxy-5-quinolyl)-α-cyanoacrylamide;
N-phenethyl β-(8-hydroxy-5-quinolyl)-α-cyanoacrylamide;
N-(4'-hydroxyphenethyl) β-(8-hydroxy-5-quinolyl)-α-cyanoacrylamide;

N-phenyl β-(3-isoquinolyl)-α-cyanoacrylamide $C_{19}H_{13}N_3O$ calculated: C 76.24 H 4.38 N 14.04 found: C 76.15 H 4.27 N 13.95
MS m/z 299.
IR cm$^{-1}$: 3500–3300 (NH); 2215 (CN); 1675, 1605 (CONH); 1580, 1530 (arom).

N-(4'-hydroxyphenyl) β-(3-isoquinolyl)-α-cyanoacrylamide;

N-benzyl β-(3-isoquinolyl)-α-cyanoacrylamide $C_{20}H_{15}N_3O$ calculated: C 76.66 H 4.83 N 13.41 found: C 76.51 H 4.75 N 13.36

MS m/z 313.
IR cm$^-$: 3500–3300 (NH); 2210 (CN); 1680, 1610 (CONH); 1585, 1530 (arom).

N-(4'-hydroxybenzyl) β-(3-isoquinolyl)-α-cyanoacrylamide;
N-phenethyl β-(3-isoquinolyl)-α-cyanoacrylamide;
N-(4'-hydroxyphenethyl) β-(3-isoquinolyl)-α-cyanoacrylamide;
N-phenyl β-(5-isoquinolyl)-α-cyanoacrylamide;
N-(4'-hydroxyphenyl) β-(5-isoquinolyl)-α-cyanoacrylamide;
N-benzyl β-(5-isoquinolyl)-α-cyanoacrylamide;
N-(4'-hydroxybenzyl) β-(5-isoquinolyl)-α-cyanoacrylamide;
N-phenethyl β-(5-isoquinolyl)-α-cyanoacrylamide;
N-(4'-hydroxyphenethyl) β-(5-isoquinolyl)-α-cyanoacrylamide;
N-phenyl β-(3-indolyl)-α-cyanoacrylamide;
N-benzyl β-(3-indolyl)-α-cyanoacrylamide;
N-phenethyl β-(3-indolyl)-α-cyanoacrylamide;
N-phenyl β-(5-hydroxy-3-indolyl)-α-cyanoacrylamide;
N-benzyl β-(5-hydroxy-3-indolyl)-α-cyanoacrylamide;
N-phenethyl β-(5-hydroxy-3-indolyl)-α-cyanoacrylamide;
N-phenyl β-(5-carboxy-3-indolyl)-α-cyanoacrylamide;
N-phenyl β-(5-carboxy-3-indolyl)-α-cyanoacrylamide;
N-phenethyl β-(5-carboxy-3-indolyl)-α-cyanoacrylamide;
N-phenyl β-(5-amino-3-indolyl)-α-cyanoacrylamide;
N-benzyl β-(5-amino-3-indolyl)-α-cyanoacrylamide;
N-phenethyl β-(5-amino-3-indolyl)-α-cyanoacrylamide;
N-(4'-hydroxyphenyl) β-(3-indolyl)-α-cyanoacrylamide;
N-(4'-hydroxybenzyl) β-(3-indolyl)-α-cyanoacrylamide;
N-(4'-hydroxyphenethyl) β-(3-indolyl)-α-cyanoacrylamide;
N-(4'-hydroxyphenyl) β-(5-hydroxy-3-indolyl)-α-cyanoacrylamide;
N-(4'-hydroxybenzyl) β-(5-hydroxy-3-indolyl)-α-cyanoacrylamide;
N-(4'-hydroxyphenethyl) β-(5-hydroxy-3-indolyl)-α-cyanoacrylamide;
N-(4'-hydroxyphenyl) β-(5-carboxy-3-indolyl)-α-cyanoacrylamide;
N-(4'-hydroxybenzyl) β-(5-carboxy-3-indolyl)-α-cyanoacrylamide;
N-(4'-hydroxyphenethyl) β-(5-carboxy-3-indolyl)-α-cyanoacrylamide;
N-(4'-hydroxyphenyl) β-(5-amino-3-indolyl)-α-cyanoacrylamide;
N-(4'-hydroxybenzyl) β-(5-amino-3-indolyl)-α-cyanoacrylamide;
N-(4'-hydroxyphenethyl) β-(5-amino-3-indolyl)-α-cyanoacrylamide;

N-phenyl β-(5-methoxy-3-indolyl)-α-cyanoacrylamide $C_{19}H_{16}N_3O_2$ calculated: C 71.68 H 5.07 N 13.20
MS m/z 318.
NMR δ ppm (DMSO): 3.82 (s, 3H), 7.09 (m, 1H), 6.88 (dd, J=2.4 and 8.8 Hz, 1H), 7.34 (m, 2H), 7.44 (d, J=8.8 Hz, 1H), 7.51 (d, J=8.8 Hz, 1H), 7.67 (m, 2H), 8.45 (s, 1H), 8.55 (s, 1H), 10.1 (bs, 1H).

N-benzyl β-(5-methoxy-3-indolyl)-α-cyanoacrylamide $C_{20}H_{18}N_3O_2$ calculated: C 72.27 H 5.96 N 12.64 found: C 72.15 H 5.35 N 12.63
MS m/z 332.

NMR δ ppm (DMSO): 3.80 (s, 3H), 4.42 (d, J=5.9 Hz, 2H), 6.87 (dd, J=2.2 and 8.8 Hz, 1H), 7.2–7.5 (m, 7H), 8.39 (s, 1H), 8.47 (s, 1H), 8.75 (t, J=5.9 Hz, 1H), 12.2 (bs, 1H).

N-(3-pyridyl) β-(4-hydroxy-5,6,7,8-tetrahydronaphth-1-yl)-α-cyanoacrylamide
N-(3-pyridyl) β-(3-indolyl)-α-cyanoacrylamide;
N-(3-pyridyl) β-(5-methoxy-3-indolyl)-α-cyanoacrylamide;
N-(3-pyridyl) β-(4-quinolyl)-α-cyanoacrylamide;
N-(3-pyridylmethyl) β-(4-hydroxy-5,6,7,8-tetrahydronaphth-1-yl)-α-cyanoacrylamide;
N-(3-pyridylmethyl) β-(3-indolyl)-α-cyanoacrylamide;

N-(3-pyridylmethyl) β-(5-methoxy-3-indolyl)-α-cyanoacrylamide $C_{19}H_{16}N_4O_2$ calculated: C 68.66 H 4.85 N 16.86 found: C 68.53 H 4.76 N 16.73

MS m/z 332.

NMR δ ppm (DMSO): 3.80 (s, 3H), 4.43 (d, J=5.9 Hz, 2H), 6.87 (dd, J=2.4 and 8.8 Hz, 1H), 7.35 (ddd, J=1.9 and 4.8 and 7.9 Hz, 1H), 7.42 (m, 2H), 7.72 (ddd, J=7.9 and 1.8 and 2.3 Hz, 1H), 8.39, 8.46 (two s, 2H), 8.45 (dd, J=1.8 and 4.8 Hz, 1H), 8.54 (dd, J=2.3 and 1.9 Hz, 1H), 8.80 (t, J=6.0 Hz, 1H), 12.2 (bs, 1H).

N-(3-pyridylmethyl) β-(4-quinolyl)-α-cyanoacrylamide;
N-(2-pyridylmethyl) β-(4-hydroxy-5,6,7,8-tetrahydronaphth-1-yl)-α-cyanoacrylamide;
N-(2-pyridylmethyl) β-(3-indolyl)-α-cyanoacrylamide;
N-(2-pyridylmethyl) β-(5-methoxy-3-indolyl)-α-cyanoacrylamide;
N-(2-pyridylmethyl) β-(4-quinoyl)-α-cyanoacrylamide.

EXAMPLE 2

N-phenyl β-(4-hydroxy-5,6,7,8-tetrahydronaphth-1-yl)-α-cyanoacrylamide

To a stirred solution of N-phenyl β-(4-methoxy-5,6,7,8-tetrahydronaphth-1-yl)-α-cyanoacrylamide (3.324 g, 0.01 mol) in anhydrous dichloromethane (100 ml) was added at −78° C. under nitrogen, over a period of 20 min, a 1M boron tribromide solution in dichloromethane (30 ml, 0.030 mol). The resulting mixture was stirred for another 1 h at −78° C. and then allowed to warm up to room temperature. After stirring for 1.5 h at room temperature the mixture was cooled to −10° C. and then quenched by dropwise addition of water (100 ml) over a 10-min period. After addition of ethyl acetate (100 ml) the organic layer was separated, washed with water, dried over $Na_2SO_4$ and evaporated under vacuum to dryness. The residue was crystallized from ethanol thus giving pure title compound in 65% yield (2.070 g).

$C_{20}H_{18}N_2O_2$ calculated: C 75.45 H 5.70 N 8.80 found: C 75.80 H 5.40 N 8.75

MS m/z 318.

IR cm$^{-1}$: 3100–3500 (NH, OH), 2210 (CN), 1685, 1610 (CONH), 1585, 1560, 1520 (C=C).

Following the above described procedure and starting from a phenolic methyl ether of formula (I), which may be obtained according to the procedure described in example 1, the corresponding phenolic compound of formula (I) may be obtained.

EXAMPLE 3

N-phenyl β-(5-amino-3-indolyl)-α-cyanoacrylamide

To a solution of N-phenyl β-(5-nitro-3-indolyl)-α-cyanoacrylamide (3.324 g, 0.010 mol) in anhydrous ethanol (200 ml) was added palladium on charcoal (0.200 g) and the mixture was hydrogenated at room temperature and atmospheric pressure until 3 equivalent of hydrogen has been taken up. The hydrogen uptake was graphed as function of time. The catalyst was filtered and the solution concentrated under vacuum until crystallization began. The mixture was cooled to 0°–5° C., filtered, the residue washed with ice-cooled ethanol and dried under vacuum. Thus almost pure title compound was obtained in about 80% yield (2.416 g). An analytical pure sample was obtained by crystallization from ethanol.

$C_{18}H_{14}N_4O$ calculated: C 71.51 H 41.67 N 18.53 found: C 71.45 H 4.55 N 18.45

MS m/z 302.

IR cm$^{-1}$: 3400, 3300 (NH), 2220 (CN), 1680, 1620 (CONH), 1590, 1510 (C=C).

Proceeding analogously and starting from a nitro compound of formula (I), which may be obtained according to the procedure described in Example 1, the corresponding amino compound of formula (I) can be obtained.

EXAMPLE 4

N-phenyl β-(4-acetoxy-5,6,7,8-tetrahydronaphth-1-yl)-α-cyanoacrylamide

To a cooled solution of N-phenyl β-(4-hydroxy-5,6,7,8-tetrahydronaphth-1-yl)-α-cyanoacrylamide (3.184 g, 0.010 mol) in dry pyridine (5 ml) was added acetic anhydride (2.040 g, 0.020 mol) and the mixture maintained at 0°–5° C. overnight. Thereupon the mixture was concentrated under vacuum, the residue dissolved in dichloromethane, the organic layer washed with water and then evaporated under reduced pressure. The crude product was crystallized from chloroform/methanol to yield pure title compound in about 80% yield.

$C_{22}H_{20}N_2O_3$ calculated: C 73.32 H 5.59 N 7.77 found: C 73.25 H 5.45 N 7.65

MS m/z 360.

IR cm$^{-1}$: 3300 (NH), 2200 (CN), 1755 (ester), 1690 (amide), 1620 (amide).

According to this procedure the phenols of formula (I) obtained in Example 1 can be transformed into the corresponding acetoxy derivatives of formula (I).

EXAMPLE 5

1,4-dihydroxy-5,6,7,8-tetrahydro-2-naphthaldehyde

To a solution of 1,4-dihydroxy-5,6,7,8-tetrahydronaphthalene (1.640 g, 0.010 mol) in dichloromethane (50 ml) was added titanium tetrachloride (5.69 g, 0.03 mol). Then 1,1-dichlorodimethyl ether (1.73 g, 0.015 mol) was added dropwise under vigorous stirring and the reaction mixture stirred for another 3 h at room temperature. Finally 5% hydrochloric acid (10 ml) was added under ice-cooling. The organic phase was separated and the residual aqueous phase repeatedly extracted with ether. The combined organic phases are washed with saturated saline solution, dried over sodium sulfate and evaporated under vacuum. The residue was crystallized from benzene or alternatively submitted to flash chromatography on silica gel with benzene/ethylacetate 85:15 to afford pure title compound in about 60% yield (1.080 g), mp 145° C.

MS m/z 180.

NMR δ ppm: 10.4 (bs, OH), 9.7 (s, CHO), 9.1 (bs, OH), 6.9 (s, H atom), 2.8 (m, 5-$CH_2$, 8-$CH_2$), 1.9 (m, 6-$CH_2$, 7-$CH_2$).

EXAMPLE 6

5-nitro-3-indolealdehyde

A mixture of N-methylformanilide (1.76 g, 0.013 mol) and phosphorous oxychloride (1.99 g, 0.013 mol) was stirred for 15 min at 20°–25° C. under nitrogen.

Then a solution of 5-nitroindole (1.62 g, 0.01 mol) in 1,2-dichloroethane (50 ml) was added and the mixture heated to reflux for 3 h. After cooling the mixture was poured onto iced water, the precipitate filtered off and washed with water. Thereupon the residue was chromatographed over silica gel using benzene/ethylacetate as eluant. Thus pure title compound was obtained in 80% yield (1.52 g).

$C_9H_6N_2O_3$ calculated: C 56.85 H 3.18 N 14.73 found: C 56.79 H ,3.01 N 14.51

MS m/z 190.

IR cm$^{-1}$: 3140, 3090 (NH), 1650 (CO), 1511, 1345 (NO$_2$).

EXAMPLE 7

N-benzyl α-cyanoacetamide

To benzylamine (1.07 g, 0.01 mol) was added methyl cyanoacetate (0.99 g, 0.01 mol) and the mixture was heated for 16 h at 100° C. without condenser to allow evaporation of the methanol formed. Cooling gave a dark red solid which was triturated with ethanol, filtered and recrystallized from ethanol to give pure title compound in about 40% yield (0.70 g). mp 123°–4° C.

MS m/z 174.

According to the above described procedure and starting from the appropriate compounds of formula (V) and of formula (VI) one can prepare the corresponding compounds of formula (III).

EXAMPLE 8

Tablets each weighing 0.150 g and containing 25 mg of the active substance, can be manufactured as follows:

composition (for 10,000 tablets):

| | |
|---|---|
| N-phenyl β-(8-hydroxy-5-quinolyl)-α-cyanoacrylamide | 250 g |
| Lactose | 800 g |
| Corn starch | 415 g |
| Talc powder | 30 g |
| Magnesium stearate | 5 g |

N-phenyl β-(8-hydroxy-5-quinolyl)-α-cyanoacrylamide, the lactose and half the corn starch are mixed; the mixture is then forced through a sieve of 0.5 mm mesh size.

Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate are added, carefully mixed and processed into tablets.

EXAMPLE 9

Capsules, each dosed at 0.200 g and containing 20 mg of the active substance can be prepared.

Composition for 500 capsules:

| | |
|---|---|
| N-benzyl β-(5-methoxy-3-indolyl)-α-cyanoacrylamide | 10 g |
| Lactose | 80 g |
| Corn starch | 5 g |
| Magnesium stearate | 5 g |

This formulation is encapsulated in two-piece hard gelatin capsules and dosed at 0.200 g for each capsule.

We claim:

1. A compound of formula (I)

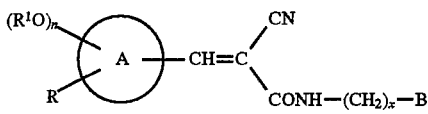

wherein
A is a bicyclic ring chosen from naphthalene and tetrahydronaphthalene,
B is a $R^2$ substituted benzene ring or an unsubstituted pyridine or thiophene ring;
R is hydrogen, $C_1$–$C_6$ alkyl, halogen, nitro, cyano, carboxy, or a group $NR^3R^4$ wherein each of $R^3$ and $R^4$ is independently hydrogen or $C_1$–$C_6$ alkyl;
$R^1$ is a hydrogen, $C_1$–$C_6$ alkyl or $C_1$–$C_6$ alkanoyl;
$R^2$ is $C_1$–$C_6$ alkyl, halogen, nitro, cyano, carboxy, hydroxy, $C_1$–$C_6$ alkoxy, $C_1$–$C_6$ alkanoyloxy or a group $NR^3R^4$ wherein $R^3$ and $R^4$ are as defined above;
n is zero or an integer of 1 to 2;
x is zero or an integer of 1 to 5;
or a pharmaceutically acceptable salt thereof.

2. A compound of formula (I), according to claim 1, wherein
A is tetrahydronaphthalene;
B is $R^2$ substituted benzene or unsubstituted pyridine;
R is hydrogen or halogen;
$R^1$ is hydrogen or methyl;
$R^2$ is hydrogen, halogen, cyano, hydroxy, carboxy or amine;
n is 0, 1 or 2; and
x is 0, 1, 2 or 3;
or a pharmaceutically acceptable salt thereof.

3. A compound of formula (I) according to claim 2, wherein
A is tetrahydronaphthalene;
B is $R^2$ substituted benzene or unsubstituted pyridine;
R is hydrogen;
$R^1$ is hydrogen or methyl;
$R^2$ is hydrogen or hydroxy;
n is 0 or 1 and
x is 0, 1 or 2,
or a pharmaceutically acceptable salt thereof.

4. A compound selected from the group consisting of the following compounds, the compound being the Z-isomer or E-isomers, or a mixture of the Z- and E-isomers:
N-phenyl β-(4-hydroxy-5,6,7,8-tetrahydronaphth-1-yl)-α-cyanoacrylamide;
N-(4'-hydroxyphenyl)-β-(4-hydroxy-5,6,7,8-tetrahydronaphth-1-yl)-α-cyanoacrylamide;
N-phenyl β-(3,4-dihydroxy-5,6,7,8-tetrahydronaphth-1-yl)-α-cyanoacrylamide;

N-(4'-hydroxyphenyl) β-(3,4-dihydroxy-5,6,7,8-tetrahydronaphth-1-yl)-α-cyanoacrylamide;

N-benzyl β-(4-hydroxy-5,6,7,8-tetrahydronaphth-1-yl)-α-cyanoacrylamide;

N-(4'-hydroxybenzyl) β-(4-hydroxy-5,6,7,8-tetrahydronaphth-1-yl)-α-cyanoacrylamide;

N-benzyl β-(3,4-dihydroxy-5,6,7,8-tetrahydronaphth-1-yl)-α-cyanoacrylamide;

N-(4-'-hydroxybenzyl) β-(3,4-dihydroxy-5,6,7,8-tetrahydronaphth-1-yl)-α-cyanoacrylamide;

N-phenethyl β-(4-hydroxy-5,6,7,8-tetrahydronaphth-1-yl)-α-cyanoacrylamide;

N-(4'-hydroxyphenethyl) β-(4-hydroxy-5,6,7,8-tetrahydronaphth-1-yl)-α-cyanoacrylamide;

N-phenethyl β-(3,4-dihydroxy-5,6,7,8-tetrahydronaphth-1-yl)-α-cyanoacrylamide;

N-(4'-hydroxyphenethyl) β-(3,4-dihydroxy-5,6,7,8-tetrahydronaphth-1-yl)-α-cyanoacrylamide;

N-phenyl β-(4-hydroxy-5,6,7,8-tetrahydronaphth-2-yl)-α-cyanoacrylamide;

N-(4'-hydroxyphenyl) β-(4-hydroxy-5,6,7,8-tetrahydronaphth-2-yl)-α-cyanoacrylamide;

N-benzyl β-(4-hydroxy-5,6,7,8-tetrahydronaphth-2-yl)-α-cyanoacrylamide;

N-(4'-hydroxybenzyl) β-(4-hydroxy-5,6,7,8-tetrahydronaphth-2-yl)-α-cyanoacrylamide;

N-phenethyl β-(4-hydroxy-5,6,7,8-tetrahydronaphth-2-yl)-α-cyanoacrylamide;

N-(4'-hydroxyphenethyl) β-(4-hydroxy-5,6,7,8-tetrahydronaphth-2-yl)-α-cyanoacrylamide;

N-phenyl β-(4-quinolyl)-α-cyanoacrylamide;

N-(3-pyridylmethyl) β-(4-hydroxy-5,6,7,8-tetrahydronaphth-1-yl)-α-cyanoacrylamide;

N-(2-pyridylmethyl) β-(4-hydroxy-5,6,7,8-tetrahydronaphth-1-yl)-α-cyanoacrylamide;

and the pharmaceutically acceptable salts thereof.

5. A process for preparing a compound of formula (I), according to claim 1, comprising the condensation of an aldehyde of formula (II)

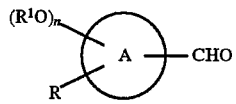

wherein A, R, $R^1$ and n are as defined in claim 1, with a compound of formula (III)

wherein $R^2$ and x are as defined in claim 1, and, if desired, converting a compound of formula (I) into another compound of formula (I), and/or, if desired, converting a compound of formula (I) into a pharmaceutically acceptable salt thereof, and/or, if desired, converting a salt into a free compound, and/or, if desired, separating a mixture of isomers of a compound of formula (I) into the single isomers.

6. A pharmaceutical composition comprising a suitable carrier and/or diluent and, as an active principle, a compound of formula (I) according to claim 1 or a pharmaceutically acceptable salt thereof.

7. Products containing a compound of formula (I) or a pharmaceutically acceptable salt thereof, according to claim 1 and an antitumor agent as a combined preparation for simultaneous, separate or sequential use in anticancer therapy.

8. A method of inhibiting tyrosine kinase activity comprising treating cells with effective an amount of the compound of claim 1, to inhibit tyrosine kinase activity in said cells.

9. A method of treating leukemia comprising administering to a patient in need thereof a pharmaceutically effective amount of a compound of claim 1.

10. A method of treating psoriasis or atheromatous plaque comprising administering to a patient in need thereof a pharmaceutically effective amount of a compound of claim 1.

* * * * *